United States Patent [19]
Sacks et al.

[11] Patent Number: 5,732,475
[45] Date of Patent: Mar. 31, 1998

[54] CIRCUMFERENCE MONITOR

[76] Inventors: Steven M. Sacks, 3925 Crow Rd., #58, Beaumont, Tex. 77706; M. Glen Kertz, 3484 Pheasant, Orange, Tex. 77630

[21] Appl. No.: 570,445

[22] Filed: Dec. 12, 1995

[51] Int. Cl.⁶ .................................................. G01B 3/10
[52] U.S. Cl. ........................... 33/555.4; 33/512; 33/514.2
[58] Field of Search ........................... 33/555.4, 512, 33/514.2, 759

[56] References Cited

U.S. PATENT DOCUMENTS

| | | | |
|---|---|---|---|
| 940,256 | 11/1909 | Kennedy et al. | 33/514.2 |
| 1,096,206 | 5/1914 | Thomas | 33/514.2 |
| 1,357,545 | 11/1920 | Bernyz | 33/514.2 |
| 2,428,980 | 10/1947 | McCann | 33/514.2 |
| 3,327,394 | 6/1967 | Tenteris . | |
| 3,621,579 | 11/1971 | Dubitsky . | |
| 3,832,780 | 9/1974 | Lewis . | |
| 3,918,166 | 11/1975 | Mason . | |
| 4,211,011 | 7/1980 | Jacobson . | |
| 4,418,477 | 12/1983 | Montgomery . | |
| 4,473,949 | 10/1984 | Schectman | 33/512 |
| 4,920,659 | 5/1990 | Becher | 33/555.4 |
| 4,974,331 | 12/1990 | Watterson | 33/514.2 |
| 5,414,943 | 5/1995 | Vogt | 33/764 |

FOREIGN PATENT DOCUMENTS 2252166  7/1992  United Kingdom .

*Primary Examiner*—Christopher W. Fulton
*Attorney, Agent, or Firm*—Conley, Rose & Tayon, P.C.

[57] ABSTRACT

The monitor for detecting changes in the circumference of an object includes a strip having an elastic portion and an inelastic portion, a self-adhesive base, an indicator guide, and one or more support guides. The strip and base together encircle the object to be monitored, forming a snug-fitting ring around the object, the strip being capable of elongating or contracting with circumference changes of the object. The inelastic portion and indicator guide includes an indicator and scale to show the changes in the dimensions of the object as the object expands or contracts.

14 Claims, 3 Drawing Sheets

CIRCUMFERENCE MONITOR

BACKGROUND OF THE INVENTION

The present invention relates generally to geometric instruments for measuring the circumference of an object, and more particularly to ring-like devices affixed to such object for continually monitoring changes in the circumference of the object over a period of time. Still more particularly, the invention relates to such devices having means thereon for indicating circumference changes.

In a variety of situations it is desirable to monitor the changes in the volume, diameter or circumference of a living object. The diagnosis or treatment of certain medical conditions, in particular, requires that the circumferential dimension of an external part of the body be measured or that changes in the circumference be monitored. A change in the volume, diameter or circumference of a part of the body frequently has important medical or personal fitness implications. Such changes include swelling of an arm or leg due to a vascular disease such as deep vein thrombosis or thrombophlebitis, or other diseases that affect vascular performance. The need for such monitoring often arises in the diagnosis and treatment of coronary disorders, liver dysfunction, compartment syndrome, kidney dysfunction or vascular disorder associated with diabetes. It is sometimes desirable to monitor changes in the abdomen during pregnancy, as part of a weight control program, or to detect an ascites condition. Ascites is a swelling of the abdomen caused by the accumulation of extracellular fluid in the abdominal cavity, and is a condition typically associated with liver dysfunction.

In cases of deep vein thrombosis or thrombophlebitis, blood flow through the vascular system is impaired due to some form of trauma, a restriction such as a blood clot, or other ailment. This causes blood and other fluids to rapidly accumulate in a given part of the body, and such accumulation causes the body part to swell. The swelling and associated vascular trauma also tends to increase sensitivity to touch in the affected area causing the patient a great deal of pain. Monitoring this swelling is a prime indicator used in determining the extent of vascular disease or trauma. Typically deep vein thrombosis and thrombosis phlebitis affect the legs.

Traditionally, methods of monitoring the progress of these diseases include the use of a standard flexible tape measure wherein a site on the calf of the affected leg is chosen and a series of measurements of the circumference of that part of the leg are taken over a period of time. Measurements are taken as often as needed, sometimes several times a day in a hospital setting. This requires slipping the tape around the affected leg and positioning it to the desired location, tensioning the tape around the leg and recording the measurement. The use of a tape measure, the most common method in present day use, presents two primary drawbacks for the clinician. As the measurements are taken over the course of several days, or even weeks, several individuals are usually involved in taking the measurements. It is difficult for two people to exactly position a tape measure at the same location on a limb, pull the tape to the same amount of tension, and get repeatable measurements. This adds a degree of error into the evaluation process and makes accurate evaluation difficult.

A second method in conventional use for monitoring changes caused by swelling is volumetric measurement. This involves placing the limb or body part to be evaluated in a volumetric container or tank containing a fluid of a known volume. The difference in the volume after insertion of the limb or body part, i.e., the displacement of fluid in the tank, gives a very accurate volumetric measurement of the affected area. This process is repeated each time a measurement is to be taken, and, as with the procedure using a tape measure, the process is prone to error. One source of error includes the limitation of accurately and repeatedly positioning the limb or body part in the volumetric container. The process is time consuming, requires cumbersome equipment, and can be stressful and painful to the patient.

Another medical need for body-monitoring occurs in certain problem pregnancies and liver dysfunction conditions where it is desirable to monitor abdominal size. This can often indicate excessive fluid retention or the accumulation of ascites, a disorder typically associated with extreme liver dysfunction, causing excessive fluid pooling in the abdominal area. Both of these conditions are usually monitored by using a standard flexible tape measure. The tape is placed around the girth of the abdomen to be measured, tensioned and the measurement recorded. As previously stated, it is difficult to repeatedly measure the same area and get accurate readings. Patients suffering from problem pregnancy or an ascites condition are usually bed-ridden, which increases the difficulty of getting a conventional tape measure around the abdomen and of obtaining accurate repeated measurements. This is a major concern with ascites conditions, as these patients are often bearing excessive weight. These factors, combined with concern for the patient's comfort, make conventional measurement procedures error prone and difficult for all concerned.

Another area where measurement of the external body is desired is in the sport of weight lifting, where athletes seek to increase muscle mass by repeatedly stressing muscle groups by strenuous exercise. This exercise produces what is referred to as a "pump" in the muscle group, which is, in effect, a swelling of the muscle due to increased blood flow and accumulation. This blood flow increase and associated swelling is the body's natural response to the increased oxygen demand that has been placed on the muscle group and the controlled damage to the muscle that is a result of the exercise. Typically, monitoring the development or extent of the "pump" is accomplished by measuring the muscle group with a standard flexible tape measure at the start of an exercise session and repeating this process at the end of the session. This change in these two measurements indicates the degree of "pump" that was achieved. There are no adequate methods for monitoring the actual development of the "pump" during the exercise process as it has been impractical to hold a flexible tape to the desired location during the exercise program. This method also presents the same errors as described above in that positioning the tape in exactly the same location for each measurement is difficult.

There have been many devices designed for measuring the circumference or girth of various body parts. Such devices are typically suitable for taking single measurements and do not provide for continual monitoring. They require that the device be placed or positioned, measurements taken and then that the device be removed. When subsequent measurements are required the entire process must be repeated.

One such single use device, disclosed in U.S. Pat. No. 3,327,394 to Tenteris, is an apparatus for measuring an appendage such as a leg using a series of transverse strips, each appropriately marked, connected at specific sites to a longitudinal base. U.S. Pat. No. 3,621,579 to Dubitsky discloses a flexible tape measuring device that can be affixed to a surface by means of an adhesive backing.

U.S. Pat. No. 3,918,166 to Mason discloses a device for measuring the circumference of the head by means of a flexible tape, that expands and contracts by means of a tensioned spring device on a closed elastic ring. That device is held in place by a tensioned spring in the expandable portion of the ring.

U. S. Pat. No. 4,418,477 Jacobson discloses a device for measuring several points on the trunk of the body by means of a plurality of transverse mounted measuring tapes that are incorporated into a wearable garment.

U.S. Pat. No. 4,418,477 to Montgomery discloses a reusable device for measuring various body parts consisting of a suitable marked paper measuring tape that slips through an indicator guide. The tape is positioned around the part to be measured and the free end of the tape is slipped through an opening in the indicator guide.

U.S. Pat. No. 4,974,331 to Waiterson discloses a device for measuring the circumference of several points along a longitudinal portion of the body. This device employs a plurality of measuring tapes attached to a drawbar.

U.S. Pat. No. 5,414,943 to Vagt discloses another device for obtaining anatomical measurements.

U.K. Patent Application GB 2,252,166 A to Harrison discloses a device for obtaining an accurate measurement of ring size. That device consists of a flexible strip of material with appropriate indicia, and a buckle arrangement that allows the strip to be formed into a ring, slipped onto a finger and tightened to indicate the user's ring size.

Although it is desirable to monitor parts of the body that are subject to swelling, growth or atrophy, none of the existing devices and methods provide an adequate way of conveniently and comfortably monitoring volume, diameter or circumference changes in parts of the external body. A device that can remain in place during the desired monitoring interval, is more accurate in detecting circumference increases or decreases, provides more comfort for the user, is sterilizable, and is in other ways suitable for medical use, would be welcomed by the health care and personal fitness industries, in particular.

SUMMARY OF THE INVENTION

The present invention provides a simple to use monitor for accurately indicating increases or decreases in the circumference of an object. The monitor may be made of sterilizable, disposable or nondisposable materials and comprises a housing that encloses and anchors the elastic end of a belt or strap-like tension strip that wraps around the object to form a closed ring.

The tension strip is attached to the housing by a breakaway safety tab that releases the monitor should the circumference of the object increase beyond the limits of the monitor. The tension strip has a resilient or elastic portion and a non-stretchable portion with a graduated scale marked on its surface. The graduated scale may be in units of length. With the tension strip encircling the object to be monitored and attached at both ends to the housing, the tension strip lengthens and contracts as pressure is exerted or decreased by the enlarging or shrinking object, based on the resiliency of the elastic.

The tension strip is able to slide in and out of the housing and through a circumference indicator guide and support guide, with any increase or decrease in the object's circumference being indicated. A clinician can view the net circumference change at whatever intervals are desired.

The present invention offers a number of features and advantages over conventional methods and apparatus for measuring circumference changes. One advantage is that it allows for continual monitoring without necessitating repeated measurements with a tape measure, thereby affording greater accuracy than has been possible in the past. The monitor is particularly suitable for use on the external human body for medical applications. By adjustment of the elasticity, width and length of the monitor, it is also appropriate for use as an exercise aid, serving to applying tension to selected muscle groups and thus increasing resistance during exercise. The monitor of the present invention may be easily adapted for use on various other objects, such as a tree trunk, for example, where monitoring of circumferential tree growth is is desirable.

Other objects and advantages of the invention will appear from the following description.

BRIEF DESCRIPTION OF THE DRAWINGS

For a detailed description of a preferred embodiment of the invention, reference will now be made to the accompanying drawings wherein.

DETAILED DESCRIPTION OF THE PREFERRED EMBODIMENT

Figure 1:
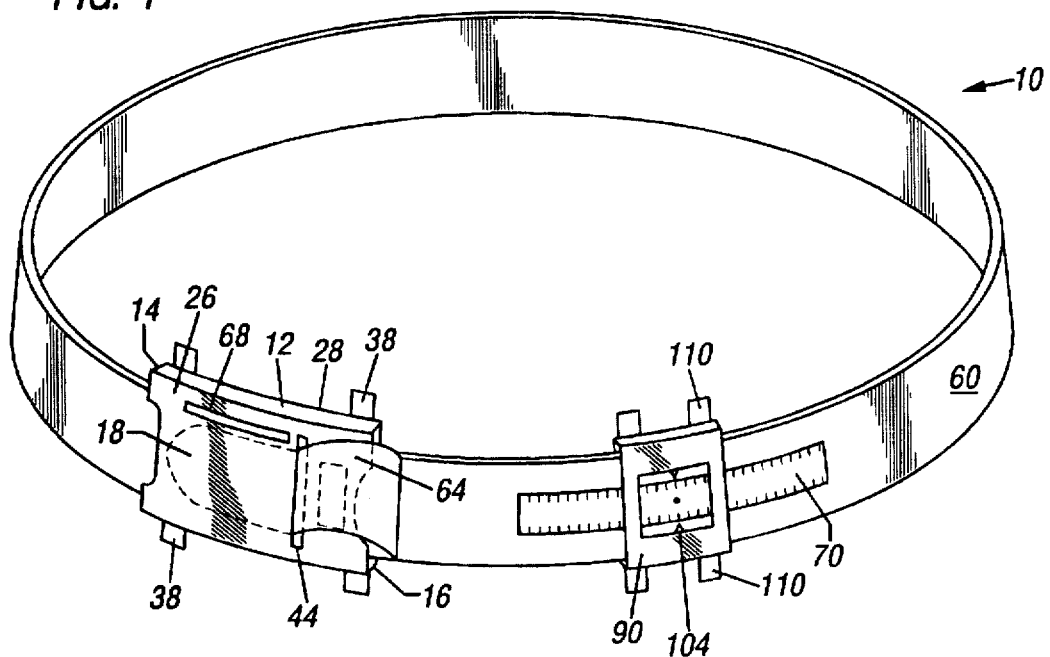
FIG. 1 is a perspective view of the monitor of the present invention shown in the closed loop position.

Referring initially to FIG. 1, there is shown an exemplary monitor 10 that is illustrative of the monitor and method of the present invention. Monitor 10 includes a base 12, a tension strip 60, which together with base 12 forms a closed loop about the object to be monitored, and an indicator guide 90 mounted on the object being monitored. When the circumference of the object expands or contracts, the degree of expansion or contraction of tension strip 60 is shown on a graduated scale 70 on strip 60 by means of a fixed reference point 104 on indicator guide 90.

Base

Figure 2:
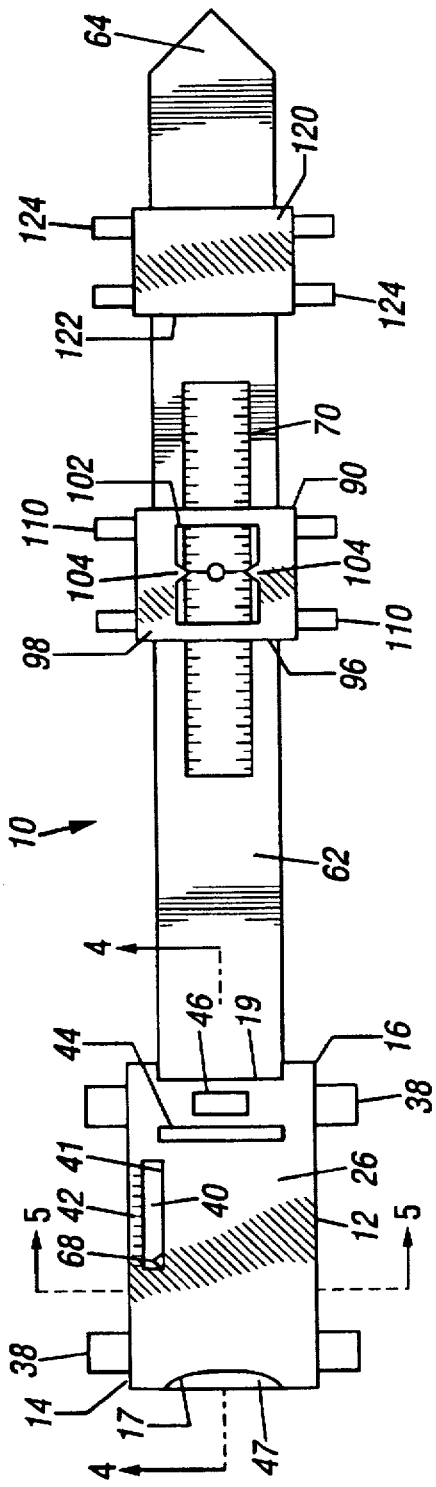
FIG. 2 is a top view of the preferred embodiment of the monitor of the present invention.

Referring now to FIG. 2, monitor 10 includes a substantially flat, rectangular base 12 made of a flexible, non-stretchable material such as paper or plastic. A preferred embodiment of base 12 is made of Tyvek™ manufactured and sold by DuPont of Wilmington, Del. Base 12 is generally flat and elongated having a top wall 26 and a bottom wall 28 adjacent the object to be monitored. Base 12 includes ends 14, 16 and one or more channels or apertures 47 that extend between walls 26,28 from end 14 to end 16. Affixed to bottom wall 28 of base 12 are adhesive tabs 38 for removably securing base 12 to the object to be monitored as hereinafter described. On top wall 26 near end 16 is a horizontal slot 44 and adjacent slot 44 is a longitudinally oriented tension indicator window 40. A tension indicator scale 42 is printed or affixed to top wall 26 of base 12 along one of the longitudinal edges 41 of window 40 and includes appropriately marked graduations. Securing means, such as adhesive pad 46, is affixed near end 16 of top wall 26 of base 12. Although a self-adhesive securing means is preferred, a buckle, Velcro™, pinch clamp or other means may be substituted. Top wall 26 may also include a notch 17 at end 14 and a notch 19 at end 16.

Figure 4:
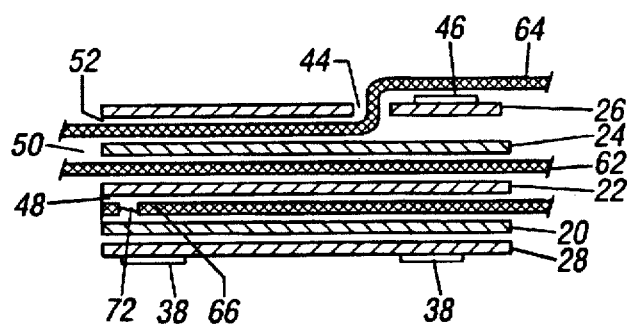
FIG. 4 is an enlarged partial cross sectional side view of the base of the monitor shown in FIG. 2, taken along plane 4—4, showing the arrangement of guide channels and the routing of the strip through the base.
Figure 5:
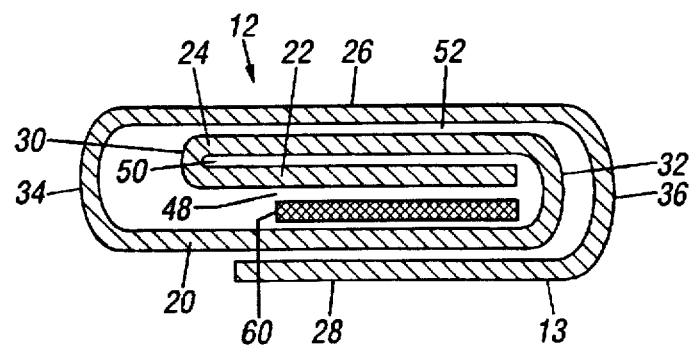
FIG. 5 is an enlarged cross sectional end view of the base shown in FIG. 2, taken along plane 5—5 showing three guide chambers through the base.
Figure 6:
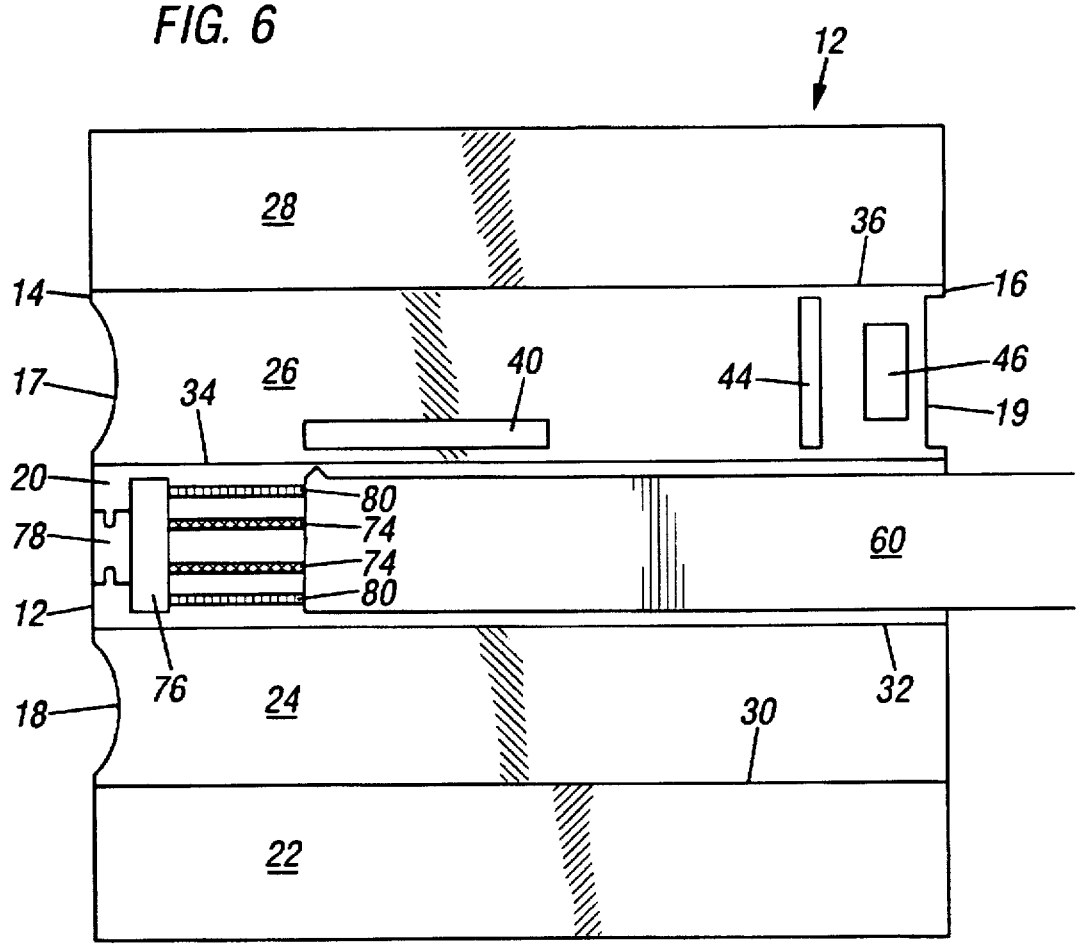
FIG. 6 is a plan view of the base shown in FIG. 5 in its unfolded configuration.

Referring now to FIGS. 4–6, the most preferred embodiment of base 12 is constructed of a single rectangular sheet of Tyvek™ forming five panels, namely central panel or wall 20, lower medial panel or wall 24, lower end panel or wall 22, upper medial panel or top wall 26, and upper end panel (bottom wall) 28, which serves as a flap. Panels 22,24 together form middle guide channel 50. Central panel 20, and lower end panel 22 together form lower guide channel 48. Lower medial panel 24 and top wall 26 together form top channel 52. Bottom wall 28 tucks under and joins to central panel 20.

The aperture 47 through base 12 may include one, two, or three flat, rectangular channels. In a preferred embodiment having lower, middle and top guide channels 50,48,52, respectively, wall 20 of base 12 is also the bottom of lower guide channel 48. Wall 22 serves as the upper boundary of lower guide channel 48 and also serves as the bottom of middle guide channel 50. Wall 24, having notch 18 at end 14, is the upper boundary of middle guide channel 50 and the base of top guide channel 52. The upper boundary of top guide channel 52 is top wall 26. Top wall 26 has a horizontal slot 44, window 40 and adhesive pad 46. Middle channel 50 is open at both ends and is narrower than lower channel 48 or top channel 52, which are of approximately equal width and may be closed at end 16.

Tension Strip

Figure 3:
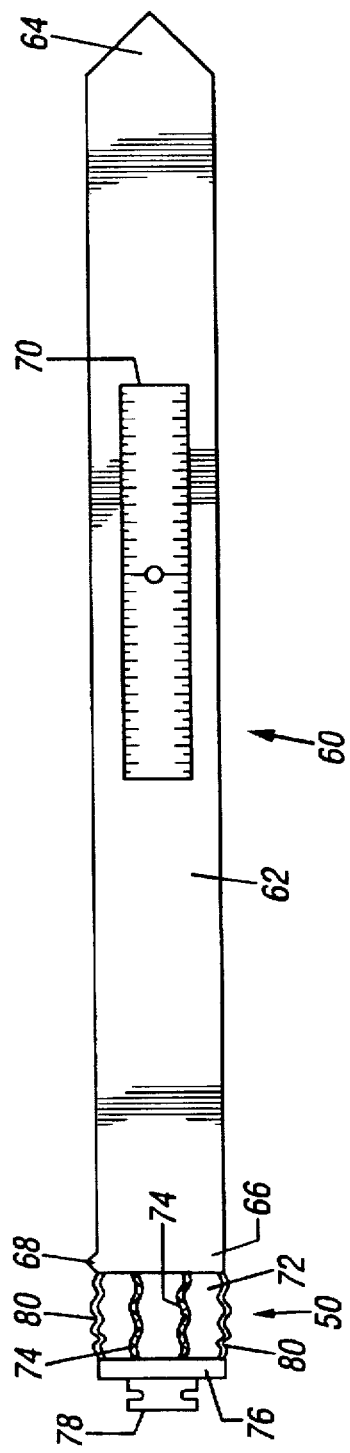
FIG. 3 is a top view of the tension strip of the monitor shown in FIG. 2.

As best shown in FIG. 3, tension strip 60 has an elastic portion 72 and an inelastic portion 62. Elastic portion 72 comprises one or more elastic inserts 74, an elastic anchor 76, a breakaway safety tab 78 and expansion stops 80. Inelastic portion 62 may be made of the same material as base 12 or of another inelastic material that is capable of being attached to inserts 74 and expansion stops 80 by gluing, heat bonding, sewing or other suitable means. Expansion inserts 74 are preferably rubber, but they may be any other suitably stretchable material such as cloth, plastic, metal or a combination of materials. Elastic inserts 74 are preferably in the form of two elastic strips, but may be a single band of stretchable material or a plurality of thin strips, as long as inserts 74 permits the appropriate amount of lengthening and retraction of tension strip 60 when used to monitor the circumference changes of an object. Attached to one end of elastic inserts 74 is elastic anchor 76, which is a narrow piece or band of flexible or inflexible material. Elastic anchor 76 is preferably made of the same material as base 12, but may be made of any suitable flexible or inflexible material that can be attached to inserts 74 by gluing, heat bonding, sewing or other suitable means. One or more expansion stops 80 are attached to elastic anchor 76 adjacent elastic inserts 74 and are strips of flexible non-elastic material, such as paper or plastic filament, that are longer than the initial length of elastic inserts 74 and may be folded or compressed lengthwise. Expansion stops 80 are also attached to elastic anchor 76 by gluing, heat bonding, sewing or the like. Similarly attached to elastic anchor 76 opposite elastic inserts 74 and expansion stops 80 is break-away safety tab 78, which is made of paper, plastic or any other material of suitable strength. Elastic portion 72 is anchored to wall 20 by break-away safety tab 78 inside end 14 of base 12 by gluing, heat bonding, sewing or the like.

The inelastic portion 62 of tension strip 60 has a leading or free end (64, preferably tapered, and another end 66. Adjacent end 66 is a projecting portion forming a tension arrow 68, which may be made of the same material as, and formed integrally with, inelastic portion 62 or may be of a rigid material such as plastic and glued to inelastic portion 62. Arrow 68 is positioned adjacent end 66 where it may be viewed in window 40 upon assembly with base 12. Elastic inserts 74 are attached to end 66 opposite elastic anchor 76.

Tension strip 60 also has a suitably positioned indicator scale 70 affixed or printed longitudinally thereon, displaying appropriate increments of linear measure such as fractions of inches or centimeters, as appropriate for the intended use. The beginning point of circumference indicator scale 70 is preferably at end 66 and scale 70 may continue for from several inches to the entire length of inelastic portion 62, as appropriate for the intended use.

Indicator Guide

Figure 7:
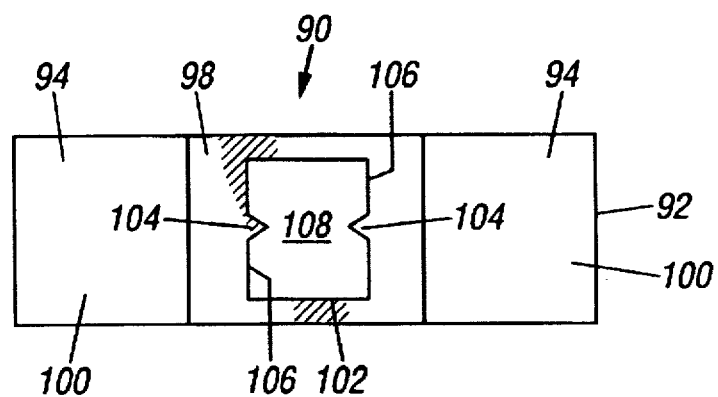
FIG. 7 is a plan view of the indicator guide of FIG. 1 in its unfolded configuration.

As depicted in FIGS. 2 and 7, indicator guide 90 is slidably disposed on tension strip 60. Indicator guide 90 is an essentially flat, rectangular member having an aperture 96 for slidingly receiving inelastic portion 62 and permitting inelastic portion 62 to slide freely therethrough. Adhesive tabs 110 are positioned on the back surface 100 of indicator guide 90 for adhering to the object to be monitored. A window 102 is provided on indicator guide 90 for viewing indicator scale 70 on strip 60 and one or two indicator pointers 104 aligned and centered along the longitudinal edges 106 of window 102. Referring now to FIG. 7, there is shown the indicator guide 90 of the preferred embodiment shown in FIG. 3 in its unfolded configuration and, without adhesive tabs 110 attached. Indicator guide 90 is constructed from an approximately 1 5/16"×3" strip by Tyvek™ by making a fold near each end 62 and bringing the ends 94 together to form an approximately 1 5/16×1 7/16" sleeve or aperture 96. A window 102 measuring approximately 3/4"×7/8" is cut in the front surface 98 of indicator guide 90 and pointers 104 are centrally positioned along the 3/4" window margins 106. Preferably, another 1 5/16"×1 7/16" piece of Tyvek™, guide liner 108, is glued over ends 94 to close and reinforce indicator guide 90 and to make a smoother path for inelastic portion 62 to slide through aperture 96. Adhesive tabs 110 are attached to ends 94, which together form surface 100 of guide 90.

Support Guides

Referring to FIG. 2, monitor 10 also includes one or more flat, rectangular support guides 120, each having an aperture 122 through which strip 60 can freely move. Attached to support guide 120 are one or more adhesive tabs 124 for removably attaching guide 120 to the object to be monitored. Support guides 120 of the preferred embodiment are made similarly to indicator guide 90, except no window is required.

Referring again to FIGS. 4–6, the preferred embodiment of base 12 is assembled by folding a single 5"×1 7/8" rectangular Tyvek™ sheet 13 into five panels. Panels or walls 20,22,24,26,28 are formed by folding inwardly along lines 30,32,34,36. Central panel 20 and upper medial panel 26 each measure about 5"×1 7/8" and panels 22,24,28 each measure about 5"×1 1/2". Panel 20 serves as the bottom of lower guide channel 48 and safety tab 78 of strip 60 is attached to central panel 20. With strip 60 extending over wall 20 from end 14, assembly of base 12 is continued. Lower end panel 22 and lower medial panel 24 are brought together, forming middle guide channel 50, and lower end panel 22 is placed over strip 60 and panel 20, thereby enclosing elastic portion 72 within lower guide channel 48.

Top guide channel 52 is formed when top wall 26 is brought down over lower medial panel 24 of middle guide channel 50. Bottom wall 28, having an adhesive layer or adhesive tabs 38, is tucked under and attached to central panel 20 to hold base 12 together. Although it is preferred that base 12 have three guide channels 48,50,52 in order to keep strip 60 from rubbing against itself or tangling as it moves within aperture 47 of base 12, alternative embodiments may combine middle and top channels 50,52. After folding, lines 30,32,34,36 define the corresponding longitudinal edges of each guide channel. In FIG. 5, however, the edges 30,32, 34,36 are depicted as expanded and rounded in order to show the continuity of sheet 13 from which base 12 of the preferred embodiment is constructed.

Tension strip 60, described hereinabove, is preferably about 1⅜" wide and about 21" long, but may be of any length required for a particular application. Elastic inserts 74 may be 2–3" long or of suitable predetermined dimensions as required for a particular use. Because base 12 serves as a shield for elastic inserts 74 and extension stops 80 during use, the length of base 12 may be other than about 5", as long as it is able to accommodate elastic portion 62 when fully extended.

Use of the Monitor

For the purpose of illustration, the monitor 10 of the present invention will be described for monitoring the swelling of a leg caused by deep vein thrombosis or phlebitis. Base 12 is positioned at an appropriate location on the leg and is affixed thereto by self-adhesive tabs 38. Base 12 is positioned on the leg in such a way that the indicator scale 70 on strip 60 and indicator guide 90 will be visible to the clinician during the monitoring period. Indicator guide 90 and one or more support guides 120 are properly oriented and slid onto inelastic portion 62 of tension strip 60, which extends through channel 48 of base 12 from safety tab 78 at end 14 to an exit point at end 16.

After looping tension strip 60 around the leg, free end 64, then reenters base 12 at end 14 via notch 18 of middle guide channel 50, and is pushed thorough channel 50 and exits base 12 at end 16. Middle guide channel 50 is narrower than channels 48 or 50 and is secured in base 12 in such a way that middle guide channel 50 does not shift or otherwise obscure the view of tension arrow 68 through window 40. If the clinician determines that additional support is needed for circumference monitor 10 to prevent it from shifting its position on the leg, more than one support guide 120 can be slid onto tension strip 60 before securing the free end 64 of strip 60 to base 12.

Free end 64 is then pulled to the desired tension as indicated by viewing tension arrow 68 through window 40 on tension indicator scale 42. The amount of preset tension should be sufficient to stretch inserts 74 and permit strip 60 to fit the leg closely and allow strip 60 to be lengthened or shortened in accordance with the elastic characteristics of inserts 74, in response to circumferential changes of the leg. Preferably inserts 74 will stretch and contract approximately linearly in correspondence with the increased or decreased tension experienced during the monitoring period, permitting the user to quantitate the amount of increase or decrease. If only qualitative changes are to be monitored, i.e., whether there is an increase or decrease in the size of the leg, but no precise distance measurements are to be made, the elastic characteristics of inserts 74 may be other than linear.

The choice of material from which elastic inserts 74 are made, and the dimensions of inserts 74, which determine the elastic limit of inserts 74, are predetermined according to the amount of force anticipated for a particular use of monitor 10. Elastic inserts 74 lengthen in proportion to the force applied along strip 60 by the swelling or contracting of the leg, and preferably in direct proportion. The "elastic limit" is the point at which elongation of a stretchable material no longer varies linearly with the increasing amount of force applied. If the stretching characteristics of elastic inserts 74 are other than linear, the graduations on tension scale 42 are circumference scale 70 may be scaled accordingly.

Best shown in FIG. 1, while maintaining the desired tension, free end 64 is folded back over and secured to base 12 by adhesive pad 46, which may be similar to adhesive tabs 38 and 110, or free end 64 may be secured by some other means of attachment such as Velcro™, a buckle or a pinch clamp, if desired. Free end 64 of tension strip 60 is then inserted into storage slot 44 on top wall 26 near end 16 of base 12 for storage within top guide channel 52 while the monitor is in use, or, alternatively, the excess length may be removed.

Indicator guide 90 is then slid along tension strip 60 to the desired position on the leg so that indicator pointers 104 of window 102 are positioned to read "zero" on scale 70, whereupon guide 90 is affixed to the leg by adhesive tabs 110. Preferably, indicator guide 90 and scale 70 are positioned adjacent end 66 of strip 60, however other embodiments may eliminate indicator guide 90 and employ end 16 of base 12 in place of indicator pointers 104. Each support guide 120 is positioned as necessary and affixed to the leg with adhesive tabs 32, permitting strip 60 to slide lengthwise through guide 90 while being prevented from shifting in other directions. The number of support guides 120 that are used to secure strip 60 to the leg may vary, depending on the particular way the monitor is being used. For example, more support guides 120 are necessary for large objects to be monitored requiring longer versions of strip 60.

As swelling of the leg occurs, the diameter and the circumference of the loop defined by strip 60 and base 12 increase, causing elastic inserts 74 to stretch in proportion to the force, thereby extending the elastic portion 72 of strip 60 within base 12. As elastic inserts 74 stretch, expansion stops 80, which are initially pleated, folded or compressed along their length, also extend as the distance between elastic anchor 76 and safety tab 78 increases. The length of expansion stops 80 is predetermined by the maker to establish the limit that elastic inserts 74 can stretch. This length is less than or equal to the length of elastic inserts 74 at the limit of its elasticity. When swelling of the leg decreases, elastic inserts 74 responds by contracting in proportion to the decreased force and expansion stops 80 slacken and blouse within lower guide channel 48. The limit of ability of monitor 10 to reflect a decrease in size of the leg from the initial condition is determined by the amount of preset tension that is applied to inserts 74 when the monitor 10 is attached to the leg. Any change in circumference of the leg is read by the clinician by viewing the position of pointer 104 relative to scale 70 on tension strip 60. Monitor 10 may remain in place on the leg for as long as the clinician determines is appropriate, preferably no more than 3–5 days, during which time periodic readings are taken, and afterwards monitor 10 is removed from the patient.

In the event that swelling of the leg exceeds the monitoring limit of monitor 10, expansion stops 80 become fully extended and form a taut connection between elastic anchor 76 and end 66. To prevent monitor 10 from constricting the leg excessively in such an event, upon reaching a certain predetermined amount of tension, breakaway safety tab 78 will tear or otherwise disengage from base 12, releasing monitor 10 from the patient's leg. The amount of tension on tension strip 60 necessary to break or disengage safety tab 78 may vary according to the requirements of a particular use. Safety tab 78 functions as the "weak link in the chain" after elastic inserts 74 have reached their elastic limit and expansion stops 80 have been fully extended. A suitable material for safety tab 78 is one that will break or tear away from base 12 after elastic inserts 74 extend to their maximum predetermined elastic limit and expansion stops 80 become fully extended, at which point the additional force exerted by the swelling leg is exerted on safety tab 78.

Monitor 10 may be sterilizable and water proof, and for certain applications may also be UV resistant. For medical applications, monitor 10 is preferably made to be used over a 3 to 5 day period and then discarded. A preferred embodiment of the present invention provides for detection of variations in length of strip 60 of as little as 2 mm. Adhesive tabs 32,38,110 and adhesive pad 46 are preferably conventional self-adhesive tape with peel off backing.

While the preferred embodiment of the invention has been shown and described, modifications thereof can be made by one skilled in the art without departing from the spirit and teachings of the invention. The embodiment described herein is exemplary only, and is not limiting. Many variations and modifications of the invention and apparatus disclosed herein are possible and are within the scope of the invention. Accordingly, the scope of protection is not limited by the description set out above, but is only limited by the claims which follow, that scope including all equivalents of the subject matter of the claims.

What is claimed is:

1. An apparatus for monitoring changes in circumference of an object comprising:
    an elongated member with ends and an elastic portion, said elongated member being adapted for being affixed to the object at one point;
    an indicator member adapted for being affixed to the object;
    said elongated member and indicator member having associated graduations and a scale thereon;
    said elongated member adapted for extending around the object and having said ends connected whereby said graduations and scale provide an indication of the change in circumference of the object as said elastic portion expands and contracts with the object.

2. A monitor for an expanding or contracting object comprising:
    an inelastic base adapted for being affixed at a point on said object;
    an indicator member;
    a flexible strip having an elastic portion and an inelastic portion, said elastic portion being attached to said base and said inelastic portion having a scale thereon,
    said strip forming a closed loop about the object such that said elastic portion expands or contracts in conformity with the circumferential expansion or contraction of the object, said strip being associated with said indicator member, and said scale and indicator member showing circumferential changes in the object.

3. The monitor of claim 2 further comprising at least one expansion stop connecting said elastic portion and said inelastic portion.

4. A monitor for an expanding or contracting object comprising:
    an inelastic base;
    an indicator member,
    a flexible strip having an elastic portion and an inelastic portion, said elastic portion being attached to said base and said inelastic portion having a scale thereon,
    said strip forming a closed loop about the object such that said elastic portion expands or contracts in conformity with the circumferential expansion or contraction of the object, said strip being associated with said indicator member, and said scale and indicator member showing circumferential changes in the object;
    at least one expansion stop connecting said elastic portion and said inelastic portion;
    said elastic portion comprising at least one elastic insert having two ends, an elastic anchor connected to one said end and said second end being connected to said inelastic portion, and wherein said expansion stops are longer than said elastic insert.

5. A monitor for expanding or contracting object comprising;
    an inelastic base;
    an indicator member;
    a flexible strip having an elastic portion and an inelastic portion, said elastic portion being attached to said base and said inelastic portion having a scale thereon,
    said strip forming a closed loop about the object such that said elastic portion expands or contracts in conformity with the circumferential expansion or contraction of the object, said strip being associated with said indicator member, and said scale and indicator member showing circumferential changes in the object;
    said indicator member being slidably attached to said strip and adapted for attachment to the object.

6. The monitor of claim 5 wherein said strip further comprises a free end and said base is adapted for joining to said free end whereby said strip and said base together are adapted to form a close-fitting loop about the object, said elastic portion being of sufficient elasticity to allow said strip to lengthen or retract in proportion to a force applied by the object when expanding or contracting.

7. The monitor of claim 6 wherein said elastic portion further comprises an elastic insert connected to a releasable tab, said tab being attached to said base and adapted for disconnecting said elastic portion from said base when said force reaches a predetermined amount.

8. The monitor of claim 7 wherein said base further includes two ends and an aperture extending between said ends, said aperture including an upper and a lower channel, said releasable tab being attached at one said end in said lower channel, and said upper channel comprising an upper wall having attachment means thereon adapted for securing said free end to said base, and a horizontal slot, a tension indicator window and tension scale thereon.

9. The monitor of claim 8 wherein said horizontal slot is adapted for insertion of said free end into said upper channel.

10. The monitor of claim 9 further comprising a middle channel disposed between said upper and lower channels.

11. The monitor of claim 8 wherein said inelastic portion further comprises a terminus having a tension arrow thereon and said arrow, tension window and tension scale together are adapted to show the amount of tension applied to said strip when said monitor is being positioned for monitoring the object.

12. The monitor of claim 5 wherein said indicator member comprises a flat rectangular indicator guide having a window, a pointer, and an aperture through which said inelastic portion may longitudinally slide, said indicator guide being adapted for removably attaching to an object to be monitored.

13. A monitor for expanding or contracting object comprising;

an inelastic base;

an indicator member;

a flexible strip having an elastic portion and an inelastic portion, said elastic portion being attached to said base and said inelastic portion having a scale thereon, said strip forming a closed loop about the object such that said elastic portion expands or contracts in conformity with the circumferential expansion or contraction of the object, said strip being associated with said indicator member, and said scale and indicator member showing circumferential changes in the object;

at least one support guide adapted for removable attachment to the object and slidably attached to said inelastic portion of said strip, said inelastic portion being held in place by said support guide and allowed to freely slide through said support guide along the longitudinal dimension of said strip.

14. A method of monitoring the expansion or contraction of an object, comprising the steps of:

extending an elongated member around the object;

affixing the member to the object at one point;

affixing an indicator member to the object, said indicator member being slidably disposed on the elongated member;

monitoring the change in position of the elongated member with respect to the indicator member as the object expands and contracts.

* * * * *